United States Patent [19]

Moniot et al.

[11] 4,311,644
[45] Jan. 19, 1982

[54] METHOD FOR PREPARING 10,10-DIFLUORO PROSTACYCLIN INTERMEDIATES AND NEW COMPOUNDS PRODUCED THEREBY

[75] Inventors: Jerome L. Moniot, Richboro, Pa.; Rita T. Fox, Princeton, N.J.; Peter W. Sprague, Pennington, N.J.; Martin F. Haslanger, Lambertville, N.J.

[73] Assignee: E. R. Squibb & Sons, Inc., Princeton, N.J.

[21] Appl. No.: 230,133

[22] Filed: Jan. 30, 1981

[51] Int. Cl.³ .......................................... C07D 307/935
[52] U.S. Cl. ............................. 260/346.22; 542/429; 560/120; 568/819
[58] Field of Search ................... 260/346.22; 542/429

[56] References Cited

PUBLICATIONS

Fried et al., "10,10-Difluoro-1,3-dehydroprostacyclin: A Chemically and Metabolically Stabilized Potent Prostacyclin", *J. Med. Chem.* 1980, 23, 234–237.

*Primary Examiner*—Henry R. Jiles
*Assistant Examiner*—Bernard Dentz
*Attorney, Agent, or Firm*—Lawrence S. Levinson; Burton Rodney

[57] ABSTRACT

A method is provided for preparing intermediates for use in 10,10-difluoro prostacyclin syntheses which method includes the steps of acylating ketopinic acid or its acid halide to form the corresponding ketopinoyl diene ester intermediate, subjecting the diene ester to a Diels-Alder reaction by reacting same with cyclopentendione, subjecting the resulting chiral ester intermediate to a fluorination and reduction to form the corresponding chiral ester diol intermediate, subjecting the diol to solvolysis to form the chiral triol intermediate, hydroxylating the chiral triol to form a pentol intermediate, subjecting the pentol to a ring cleavage to form the difluoro dihydroxy prostacyclin intermediate

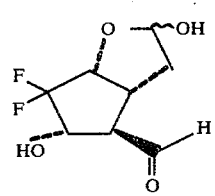

and subjecting same to a Wittig reaction to form the difluoro dihydroxy prostacyclin intermediate

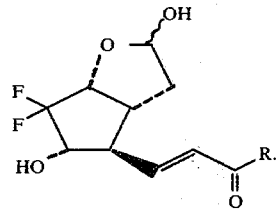

All of the above-mentioned intermediates are novel compounds and thus are also provided.

8 Claims, No Drawings

METHOD FOR PREPARING 10,10-DIFLUORO PROSTACYCLIN INTERMEDIATES AND NEW COMPOUNDS PRODUCED THEREBY

The present invention relates to a method for the production of intermediates which are useful in the production of pharmacologically active prostacyclin derivatives, such as those of the formula

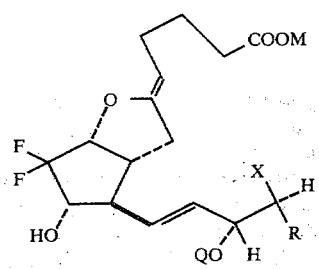

or its corresponding alkali metal salt, wherein M may be H, alkyl, aralkyl or an alkali metal; X may be H or F; Q is H or acyl; and R may be lower alkyl, lower alkenyl, aralkyl, or cycloalkyl.

The term "lower alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substituent, such as F, Br, Cl or I or $CF_3$ or a phenyl substituent.

The term "lower alkenyl" as employed herein includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy (that is, lower alkyl-O).

The term "lower alkoxy" refers to any of the above lower alkyl groups attached to an oxygen (lower alkyl-O).

The term "cycloalkyl" refers to cycloaliphatic compounds including from 5 to 7 carbons and are exemplified by cyclopentyl, cyclohexyl or cycloheptyl.

The term "acyl" as employed herein refers to "lower alkanoyl" groups, that is, any of the above lower alkyl groups attached to a carbonyl group

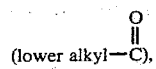

(lower alkyl—C), as well as monocyclic aroyl groups, that is, phenyl, linked to a carbonyl group, the phenyl being unsubstituted or substituted with one, two or three lower alkyl groups, halogen, hydroxy, amino or nitro.

The final compounds prepared by employing the intermediates and the method of this invention are physiologically active compounds which possess prostacyclin-like activity and thus, may be employed for the purpose of lowering elevated blood pressure and of increasing peripheral blood flow. Therefore, such compounds may be employed in the treatment of hypertension or for the relief of circulatory problems.

In addition, the compounds produced employing the method of this invention and the intermediates produced thereby prevent the aggregation of blood platelets thereby removing one of the contributory factors to the formation of atheroschlerotic plaques. As a result, such compounds may be employed in hemodialysis and during open heart surgery where it is important to prevent aggregation of platelets thereby impeding the flow of blood through the filter pads.

In addition, some of the compounds produced by employing the intermediates produced by the method of this invention cause regression of the corpus luteum, and they can therefore be used for estrus synchronization in farm animals so as to achieve greater economy in the practice of artificial insemination, or as contraceptive agents in the human female. Being protected from metabolic inactivation these compounds can be administered perorally or intravenously, in contrast to the corresponding natural prostaglandins.

Perhaps one of the most important properties of the compounds produced employing the intermediates produced by the method of this invention is the considerable chemical stability which is imparted to them by the presence of the two fluorine atoms in the 10-position. As a result of this greatly increased chemical stability, such compounds retain their biological activity considerably longer than is the case with the naturally occurring prostacyclins.

The pharmacologically active compounds produced employing the intermediates produced by the method of this invention may be administered to animal or patient being treated therewith in any manner known and convenient to the skilled worker practicing the invention, the dosage and concentration of the final product being adjusted to the requirement of the patient and the properties of the respective compound being employed. The skilled worker may prepare the final products in such composition and dosage forms as are usually employed for such purposes, depending upon the route of administration selected for the ultimate composition, for example, parenteral, peroral or topical final dosage and routes of administration.

The process of this invention entails a number of steps generally represented by the following reaction sequence.

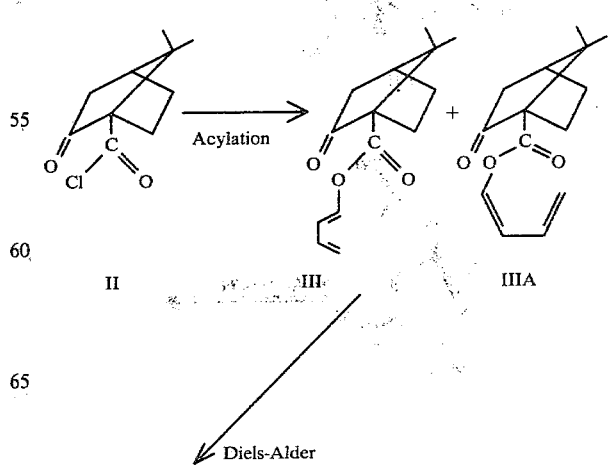

-continued

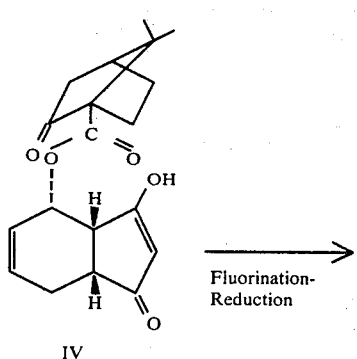

IV

Fluorination-Reduction →

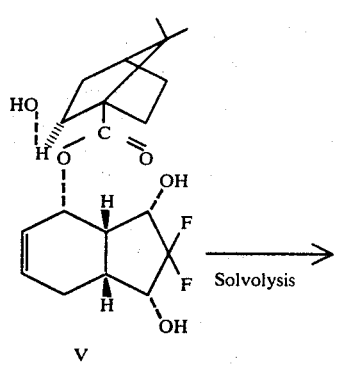

V

Solvolysis →

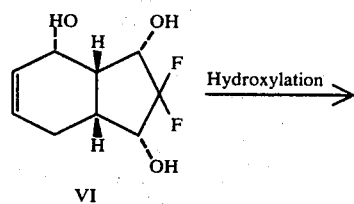

VI

Hydroxylation →

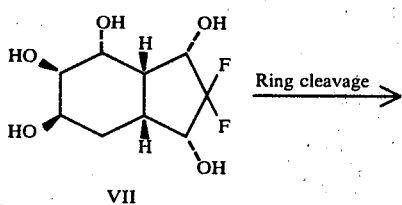

VII

Ring cleavage →

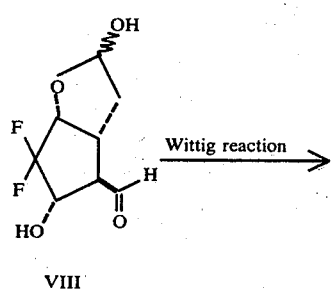

VIII

Wittig reaction →

-continued

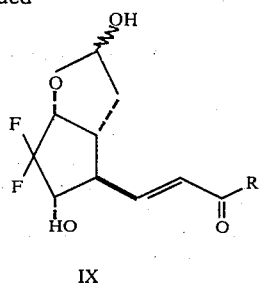

IX

In carrying out the process of the present invention as outlined in the above reaction sequence, crotonaldehyde is acylated by reaction with an acylating agent, such as, the ketopinic acid or acid halide II, such as the acid chloride, preferably the l-isomer, pinane carboxylic acid halide or (S)-malic acid halide employing a molar ratio of II:crotonaldehyde of from about 0.8:1 to about 1.5:1, preferably from about 0.9:1 to about 1:1, in the presence of an organic base, such as triethylamine, 4-(N,N-dimethylamino)pyridine, pyridine, 2,6-dimethylpyridine, or mixtures thereof, preferably under anhydrous conditions, such as under nitrogen or argon while maintaining the reaction mixture at a temperature of from about −18° to about 50° C. and preferably from about 0° to about 25° C., to form the corresponding ketopinoyl diene ester III in admixture with IIIA. The ketopinoyl diene ester III, a new intermediate, is separated from IIIA and is then converted to Diels-Alder adduct IV, which is a new intermediate, by reacting III with cyclopentendione

employing a molar ratio of III:cyclopentendione of from about 1:1 to about 2:1, and preferably from about 1.3:1 to about 1.5:1, in the presence of an inert solvent such as acetonitrile, dimethylformamide or dimethylacetamide, to form the chiral ester adduct IV.

The novel chiral ester adduct IV is then fluorinated by reaction with, for example, perchloryl fluoride (molar ratio of fluoride:IV of from about 2:1 to about 50:1, preferably from about 3:1 to about 10:1) in the presence of a weak base, such as sodium or potassium bicarbonate, at a temperature of from about −25° to about 30° C., preferably from about −25° to about 0° C. The intermediate difluoro derivative V resulting from this reaction is not isolated but is immediately reduced with a hydride reducing agent, such as sodium borohydride or lithium borohydride (molar ratio of hydride:difluoro compound V of from about 1:1 to about 8:1, preferably from about 2:1 to about 4:1) to form the difluoro chiral ester diol V, which is a new intermediate.

The novel diol V is treated with a strong alcoholic base, such as a mixture of sodium or potassium hydroxide in aqueous methanol and/or ethanol to form the chiral triol VI (which is a new intermediate) which is hydroxylated, for example, by reaction with osmium tetroxide, and a co-oxidant, such as N-methyl morpholine-N-oxide (molar ratio of VI:co-oxidant compound of from about 1:1 to about 1:2, preferably from about 1:1.1 to about 1:1.5, in the presence of water and an inert solvent, such as tetrahydrofuran, glyme, ethylacetate or acetone to form the pentol VII, which is a new intermediate. Thereafter, the novel pentol VII is subjected to ring cleavage, for example, by reacting same with sodium metaperiodate (molar ratio of periodate:-VII of from about 3:1 to about 2:1, preferably from about 2.5:1 to about 2.2:1) in the presence of a weak base, such as sodium or potassium bicarbonate to form VIII, which is also a new intermediate.

The novel intermediate VIII is subjected to a Wittig reaction by reacting same with a tributylphosphorane of the structure

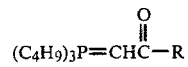

wherein R is lower alkyl, lower alkenyl, aralkyl or cycloalkyl in a molar ratio of VIII:A of within the range of from about 1:1 to about 0.5:1, preferably from about 1:1 to about 0.85:1, in the presence of an inert solvent, such as diethylether, dimethyl sulfoxide, tetrahydrofuran or glyme, to form the new prostacyclin intermediate IX.

The novel intermediate IX may then be employed in the preparation of both optically active prostaglandin and prostacyclin derivatives, as for example, in accordance with the following reaction sequence.

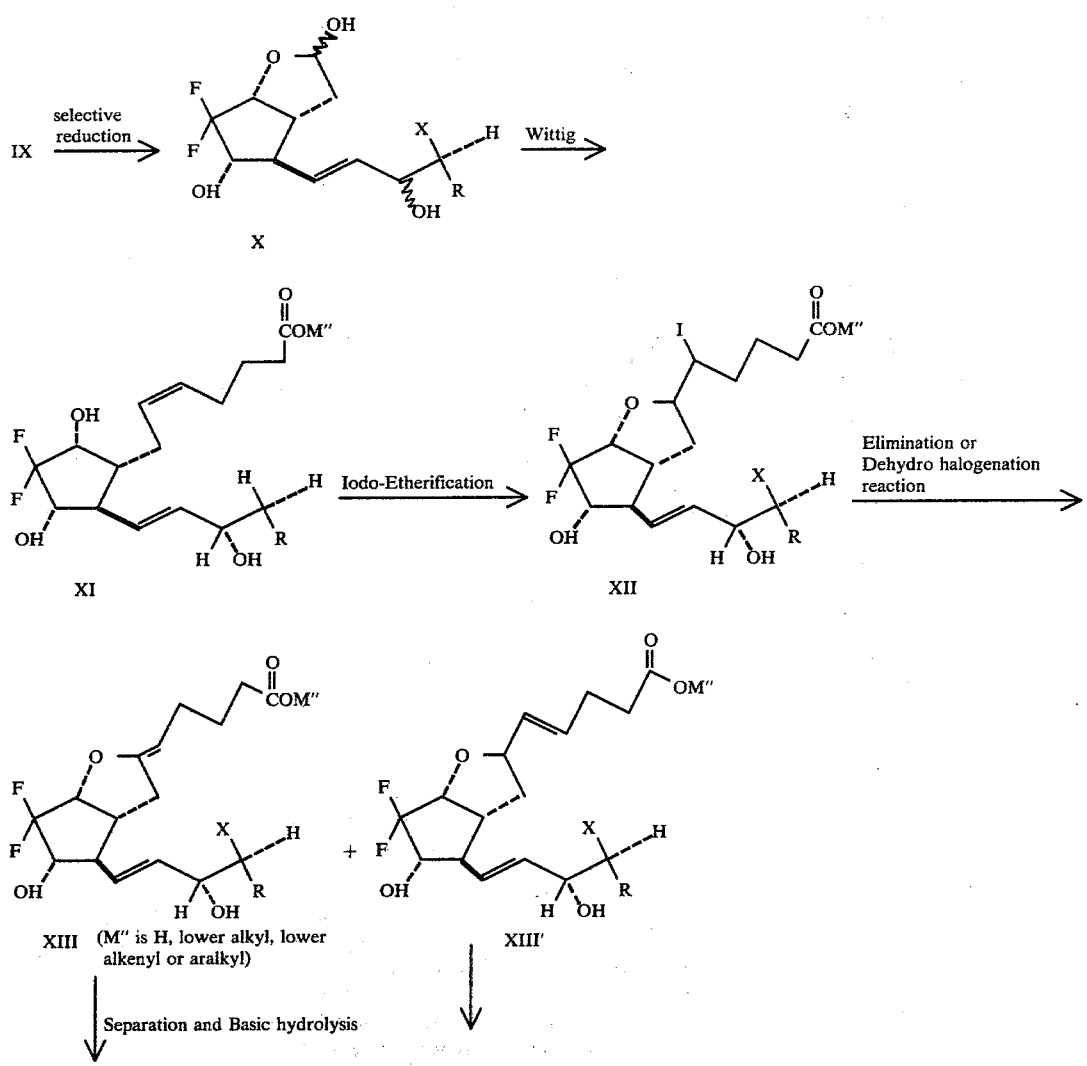

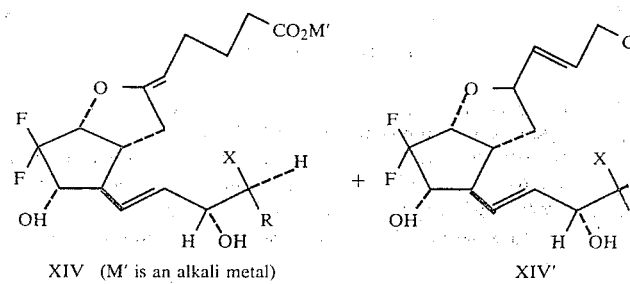

XIV (M' is an alkali metal)      XIV'

In forming the final prostacyclin products of formulae XIV and XIV', the prostacyclin intermediate IX is subjected to selective reduction by, for example, reacting same with an appropriate reducing agent, such as sodium borohydride, to form the formula X prostacyclin intermediate which is made to undergo a Wittig reaction by reacting same with a triphenylphosphonoalkanoic acid of the structure

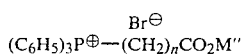

wherein M" is as defined above as well as halide ion, n is 3 or 4, in a molar ratio of X:B of from about 1:1 to about 0.2:1, in the presence of an alkali metal alkoxide, such as potassium t-butoxide and an inert solvent, such as dimethyl sulfoxide, tetrahydrofuran or glyme, and the crude prostaglandin so-formed is treated with a diazoalkane, such as $CH_2N_2$, to form the 10,10-difluoro—$PGF_{2\alpha}$ methyl ester.

The 10,10-difluoro-$PGF_{2\alpha}$ methyl ester, XI is cyclized by an iodoetherification reaction by treatment with excess halogen or halogenimide, such as iodine in the presence of a solvent, such as methylene chloride and weak base, such as sodium bicarbonate or potassium bicarbonate employing a molar ratio of XI:halogen of from about 1:1 to about 0.2:1, to form the iodoether XII.

Treatment of the iodoether XII with a base, such as diazabicyclo[5,4,0]undec-5-ene results in the formation of the prostacyclin XIII and its $\Delta^4$-isomer XIIIA in the form of their esters which comprise physiologically active end products. Additional physiologically active products are obtained by hydrolysis of the esters with, for example, sodium hydroxide, to form the corresponding salts XIV and the salts XIVA of the $\Delta^4$-isomer XIV.

It should be understood in the practice of this invention that in the preparation of the various compounds producible thereby, whenever a compound having free hydroxy groups is produced it may be further treated in accordance with methods well known in the art to provide the respective acyl derivatives thereof. Thus, a compound prepared by the method of this invention having free hydroxy groups may be treated with a suitable acylating agent, such as those derived from hydrocarbon carboxylic acids of twelve carbon atoms or less to yield the desired acyloxy derivatives as is well known to the skilled worker.

In addition to the foregoing description, it should be understood that the procedures and practices employed in the instant invention are equally applicable to the treatment and processing of other and further intermediate and starting materials to yield further final products. For example, for the many substituents, intermediates or even starting materials which may be available to and employable by the skilled worker in the practice, attention is directed to the following United States Patents, the disclosures of which are incorporated herein by reference: U.S. Pat. Nos. 4,124,599; 4,158,667; 4,174,441; 4,191,824; 4,198,230; 4,198,500, 4,202,970; 4,202,971 and 4,202,972.

Whenever in the specification and the claims appended thereto a wavy line ($\xi$) is employed in the linkage of substituents in the chemical structures set forth, it is meant to denote that the appended moiety may be either in the alpha- or beta-stereochemical configuration in the molecule.

The invention may be further illustrated by the following examples.

The following Examples represent preferred embodiments of the present invention. All temperatures are in degrees Centigrade.

EXAMPLE 1

[3aR-[3aα,4α(E),5β,6aα]]-1-(6,6-Difluorohexahydro-2,5-dihydroxy-2H-cyclopenta[b]furan-4-yl)-1-octen-3-one

A.

(1R)-7,7-Dimethyl-2-oxobicyclo[2.2.1]-heptane-1-carboxylic acid, 1,3-butadienyl ester Triethylamine (2 ml/g acid chloride) is added dropwise under nitrogen to 1-ketopinic acid chloride (~50 g) (prepared as described in Organic Synthesis, Vol. 45, p. 55), 1.1 equivalent anhydrous (distilled) crotonaldehyde, and 0.5 g 4-dimethylaminopyridine (DMAP) stirred in an ice bath. The mixture is allowed to warm to room temperature and stir overnight. An additional one equivalent of crotonaldehyde is added and the mixture stirred for another day. The solvent is removed in vacuo and the black oily residue is triturated with hexane (~500 m). The solid that is formed is filtered off and the filtrate evaporated to dryness. The residue is washed through florisil (400 ml sintered glass, funnel, half full) twice with hexane: yield (65-78%) of a clear slightly yellow oil. Single spot TLC $R_f$ 0.8; silica gel-hexane:ethyl acetate (1:1).

B.

(1R)-7,7-Dimethyl-2-oxobicyclo[2.2.1]-heptane-1-carboxylic acid, 1,3-butadienyl ester, [3aR-(3aα,4β,7aα)]-3a,4,7,7a-tetrahydro-1-hydroxy-3-oxo-3H-inden-4-yl ester The ketopinoyl diene ester prepared in Part A, cyclopentendione (0.75 equivalent), and acetonitrile (~1 ml/g of reactants) is allowed to stand over seed crystals for 10 days in the dark without stirring or shaking. The mother liquor is decanted from the solid material which is washed with ethyl acetate. The solid is dissolved in CHCL₃ which is removed in vacuo to yield an oil. The oil is crystallized by adding acetonitrile and allowing the mixture to stand: yield 59%, m.p. 159°–160°, $[\alpha]_D^{RT} = +131°$ [c=0.2, MeOH].

Further material is obtained from the decantate and ethyl acetate washings. Total yield 75–78%.

C.

(1R-exo)-2-Hydroxy-7,7-dimethylbicyclo[2.2.1]heptane-1-carboxylic acid, [1R-(1α,3α,3aβ,4α,7aβ)]-2,2-difluoro-2,3,4a,4,-7,7a-hexahydro-1,3-dihydroxy-1H-inden-4-yl ester In a flask equipped with gas inlet and outlet, stirring, thermometer and addition funnel is placed the chiral ester produced in Part B (5.0 g) and 95% ethanol (400 ml) and the solution is chilled to and maintained at 0°→5° C. Perchloryl fluoride gas is passed through the solution for 5–10 minutes before the slow dropwise addition of 60 ml of an aqueous solution containing KHCO₃ (3.1 g) is commenced (time of addition of 75 minutes). The reaction vessel is then purged with N₂ gas for 30–40 minutes and sodium borohydride (3.0 g) is added in two portions. After all gas evolution has ceased, the reaction is quenched by addition of solid NH₄Cl and filtered. The filtrate is concentrated under reduced pressure and the resulting oil is partitioned between water and ether. The organic layer is dried over MgSO₄, filtered and evaporated onto coarse silica gel and flash chromatographed on a SiO₂ column using 25% ethyl acetate in hexane as eluent to afford after one recrystallization the title compound (4.55 g, 75%), $[\alpha]_D = +6.3°$, m.p. 120°–128° C.

D.

[1R-(1α,3α,3aβ,4α,7aβ)]-2,2-Difluoro-2,3,3a,4,5,5a-hexahydro-1H-indene-1,3,4-triol To a mixture of methanol (50 ml), ethanol (50 ml) and 5% aqueous sodium hydroxide (40 ml) is added chiral ester diol ($[\alpha]_D = +6.3°$) produced in Part C, and the solution is allowed to stir under argon at room temperature for 5 hours. The solution is adjusted to pH of 6.5 with 5% aqueous hydrochloric acid, diluted with 300 ml absolute ethanol and evaporated to dryness. The residue is digested with ether/ethyl acetate (1:1) and the filtrate is concentrated to a dense oil which is flash chromatographed on SiO₂ column using 32% ethyl acetate in hexane to give after one recrystallization from 15% ethyl acetate in hexane 3.8 g of the title D compound $[\alpha]_D = +53°$ as colorless prisms, m.p. 102°–109° C. Yield=86%.

E.

[1R-(1α,3α,3aβ,4α,5β,7aα)]-2,2-Difluorooctahydro-1H-indene-1,3,4,5,6-pentol

To a stirred solution of chiral triol produced in Part D (2.64 g, 12.2 mmol) in THF (75 ml) and water (30 ml) is added N-methyl morpholine-N-oxide monohydrate (2.08 g) and 2.5 ml of an 0.5% ethereal solution of osmium tetroxide and the mixture is allowed to stir at room temperature overnight. Ethylene glycol (0.2 ml) is added to the solution along with absolute ethanol (200 ml) and the solvents are removed in vacuo at 60° C. The resulting oil is taken up in ethanol (200 ml) and the solvents are again removed in vacuo to afford crystals of the title E compound. Recrystallization from acetonitrile affords 3.005 g of the title E compound as white-tan crystals, m.p. 158°–160° C., $[\alpha]_D = -71°$ (c=1.0). Yield=98%.

F.

[3aR-(3aα,4α,5β,6aα)]-6,6-Difluorohexahydro-2,5-dihydroxy-2H-cyclopenta[b]furan-4-carboxaldehyde A solution of sodium metaperiodate (2.22 g, 10.4 mmol) in water (25 ml) is added dropwise over 30 minutes to a solution of the pentol compound produced in Part E (1.1 g, 4.16 mmol) and NaHCO₃ (2.1 g, 24.6 mmol) in water (25 ml) at room temperature and the resulting solution is stirred 1.5 hours under argon. The mixture is then poured into 5% acetonitrile in ethyl acetate (400 ml) and stirred vigorously while Na₂SO₄ (solid ~0.5 lb) is added to absorb the aqueous layer. The mixture is stirred for 10 minutes, filtered and the solids are washed with 5×200 ml of 5% acetonitrile in ethyl acetate. The combined filtrates are further dried over Na₂SO₄ and evaporated in vacuo to give the title F compound (0.85 g) as a dense non-mobile oil ($R_f$=0.23, ethyl acetate:hexane, 6:4, SiO₂ plates) in 95+% yield.

G.

[3aR-[3aα,4α(E),5β,6aα]]-1-(6,6-Difluorohexahydro-2,5-dihydroxy-2H-cyclopenta[b]furan-4-yl)-1-octen-3-one A mixture of 3A molecular sieves and 0.85 g of the [3aR-(3aα,4α,5β,6aα)]-6,6-difluorohexahydro-2,5-dihydroxy-2H-cyclopenta[b]furan-4-carboxaldehyde compound produced in Part F in ether suspension (300 ml) is stirred under argon for 10 minutes and then 2-oxoheptylidene-tri-n-butylphosphorane (1.34 g) is added all at once and the mixture is allowed to stir overnight at room temperature under argon. The mixture is filtered and the filtrate is evaporated in vacuo onto Silicar CC-7 and flash chromatographed on LP-1 silica gel using 30% ethyl acetate in hexane to give the title compound (0.657 g) 53% as a colorless dense oil $[\alpha]_D = -17.8°$ (c=1.1, MeOH). TLC; ($R_f$=0.31, SiO₂ plates using ethyl acetate:hexane, 6:4).

EXAMPLE 2

(5Z,9α,11α,13E,15S)-6,9-Epoxy-10,10-difluoro-11,15-dihydroxyprosta-5,13-dien-1-oic acid, methyl ester

A.

[3aR,[3aα,4α(E),5β,6aα]]-Difluorohexahydro-4-(3-hydroxy-1-octenyl)-2H-cyclopenta[b]furan-2,5-diol A solution of the prostacyclin produced in Example 1 (0.33 g, 1.08 mmol) in 0.4 M CeCl₃ in methanol (4 ml, 1.5 mmol), water (3 drops) and trimethylorthoformate (1.5 ml) is warmed to 35° C. under argon for four and ½ hours. The reaction mixture is chilled to 0° C. and sodium borohydride (42 mg, 1.1 mmol) is added all at once and the mixture is allowed to come to room temperature (15 minutes) and is quenched by addition of diluted aqueous HCl. The mixture is diluted with three volumes of brine, extracted with ether, the ether layer is dried over MgSO₄ and evaporated to a residue which is taken up in 8 ml of acetonitrile. To this solution is added 15 ml of 5% aqueous HCl and the mixture is warmed to 35° C. for 4 hours and allowed to stir at room temperature for 12 hours. The reaction mixture is poured into 3 volumes of brine and extracted with ether, the ether is dried over MgSO₄, filtered and evaporated onto SiO₂ and chromatographed using 1:1 ethyl acetate-hexane to give 0.27 g (82%) as a dense oil. (TLC; $R_f$=0.23, ethyl acetate-hexane, 6:4, SiO₂ plates).

B.
(5Z,9α,11α,13E,15±)-10,10-Difluoro-9,11,15-trihydroxyprosta-5,13-dien-1-oic acid, methyl ester To a stirred solution of carboxybutyltriphenylphosphonium bromide (3.23 g, 7.32 mmol) and potassium t-butoxide (1.664 g, 14.64 mmol) in freshly distilled THF (70 ml) at room temperature, under agron, is added a solution of hemi-acetal produced in Part A (0.56 g, 1.65 mmol) in THF (15 ml) and after stirring at room temperature (1.5 hour) the reaction is quenched by addition of saturated solution of NH₄Cl in 2 N HCl. The layers are separated, the aqueous layer is back extracted with ethyl acetate and the combined organic layers are dried over MgSO₄ and concentrated to a dense oil. The resulting light yellow oil is dissolved in 5% aqueous K₂CO₃ (120 ml) and extracted with ether. The aqueous layer is adjusted to pH 5 with NaHSO₄ and extracted with ether (2×100 ml) and the organic layer is dried over MgSO₄ and concentrated to a slurry of crystals which are removed by filtration. The filtrate is treated directly with excess ethereal solution of diazomethane for 15 minutes at 0° and 15 minutes at ambient temperature. After removal of the solvents, the residue is flash chromatographed on SiO₂ column using 25% ethyl acetate in hexane as the eluent to afford as the slow moving methyl ester 10,10-difluoro PGF₂α (0.212 g) (TLC; R$_f$=0.41, ethyl acetate-hexane, 6:4, SiO₂ plates); the fast moving ester 10,10-difluoro-15-epi-PGF₂α L (0.21 g), (TLC; R$_f$=0.52, ethyl acetate-hexane, 6:4, SiO₂ plates). Total yield=66%.

C.
(9α,11α,13E,15S)-6,9-Epoxy-10,10-difluoro-11,15-dihydroxy-5-iodoprost-13-en-1-oic acid, methyl ester To a solution of the former ester produced in Part B (0.19 g) in methylene chloride (4.5 ml) at room temperature is added saturated solution of KHCO₃ (1.4 ml) and solid I₂ (0.123 g) and the mixture is allowed to stir at room temperature, in the dark, under argon for 1.5 hours. The mixture is diluted with CH₂Cl₂ (30 ml) and the excess I₂ is reduced with saturated solution of Na₂SO₃ and on further dilution with CH₂Cl₂ (50 ml) the layers separated. The aqueous layer is reextracted with CH₂Cl₂ and the combined organic layers are washed with brine, dried over MgSO₄, filtered and evaporated to afford the title iodo ethers as a light yellow oil (0.16 g). Yield=66%. (TLC; R$_f$=0.43, ethyl acetate-hexane, 6:4, SiO₂ plates).

D.
(5Z,9α,11α,13E,15S)-6,9-Epoxy-10,10-difluoro-11,15-dihydroxyprosta-5,13-dien-1-oic acid, methyl ester A solution of iodo ethers produced in Part C (0.155 g) and 1,5-diaza[5,4,0]-bicycloundec-5-ene (DBU) (0.1 ml) in toluene (2 ml) is heated to 65° C. for 3½ hour, under argon. The reaction mixture is cooled and diluted with ether (100 ml) and is washed successively with half-brine, pH 5 buffer, saturated KHCO₃ solution and brine. The organic layer is dried over MgSO₄, filtered and evaporated to a residue which affords (after SiO₂ flash chromatography, ether:pentane, 3:1) 0.052 g of the title compound as a colorless oil, 45% chemical ionization mass spectrum: (M+1)⁺=m/e 4.03. (TLC; R$_f$=0.42, ethyl acetate-hexane, 6:4, SiO₂ plates).

EXAMPLE 3
(5Z,9α,11α,13E,15S)-6,9-Epoxy-10,10-difluoro-11,15-dihydroxyprosta-5,13-dien-1-oic acid, sodium salt To a mixture of 1 N NaOH (0.55 ml) and ester from Example 2 under argon at room temperature is added methanol (1 ml) and the mixture is allowed to stir for 3.5 hour. The pH is adjusted to 9 with CO₂ (dry ice) and the mixture is concentrated under vacuum (0.3 mm) to the title compound in the form of a white powder embedded in a matrix of NaHCO₃. (TLC; R$_f$=0.21, ethyl acetate-hexane, 6:4; SiO₂ plates.

What is claimed is:

1. A method for preparing 10,10-Difluoroprostacyclin intermediates of the structure

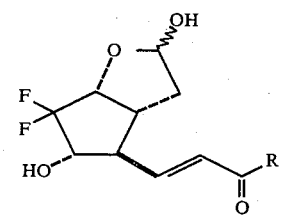

wherein R is lower alkyl, lower alkenyl, aralkyl or cycloalkyl, which includes the steps of reacting ketopinic acid or its acid halide with an acetylating agent to form a ketopinoyl diene ester intermediate of the structure

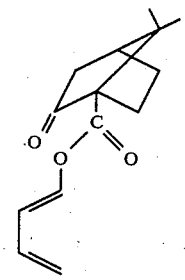

reacting the ketopinoyl diene ester with a cyclopentendione in a Diels-Alder reaction to form the Diels-Alder chiral ester adduct having the structure

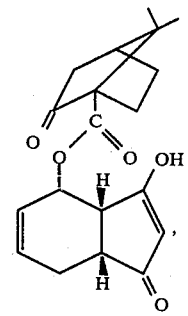

reacting the chiral ester with a fluorinating agent and then reacting the fluorinated chiral ester with a reducing agent to form the corresponding chiral ester diol of the structure

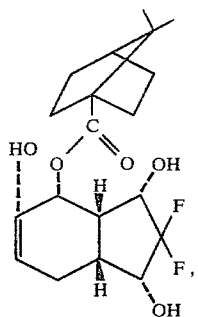

reacting the chiral ester diol with a base in the presence of an alcohol to form the chiral triol of the structure

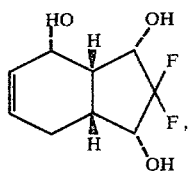

reacting the chiral triol with a hydroxylating agent to form the pentol of the structure

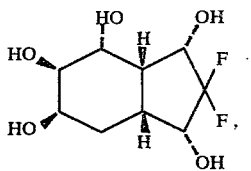

reacting the pentol with a ring cleaving agent to form the difluoro dihydroxy prostacyclin of the structure

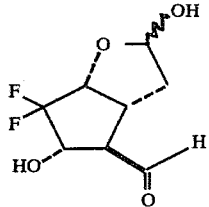

and subjecting the above prostacyclin derivative to a Wittig reaction by reacting same with a phosphonio compound of the structure

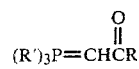

wherein R and R′ are the same or different and are lower alkyl, to form the difluoro dihydroxy prostacyclin intermediate of the structure

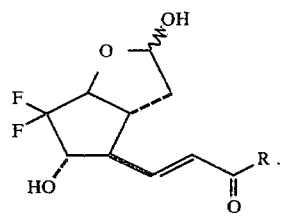

2. The method as defined in claim 1 wherein the ketopinic acid halide employed is 1-ketopinic acid chloride.

3. The method as defined in claim 1 wherein the acetylating agent employed is crotonaldehyde.

4. The method as defined in claim 1 wherein the fluorinating agent employed is perchloryl fluoride.

5. The method as defined in claim 1 wherein the hydroxylation is conducted in the presence of osmium tetroxide and a co-oxidant.

6. The method as defined in claim 1 wherein sodium metaperiodate is employed in the ring cleavage.

7. The method as defined in claim 1 wherein the phosphonio compound is

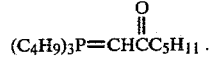

8. A prostacyclin intermediate having the structure

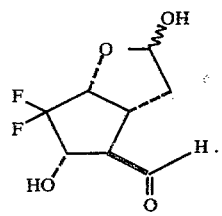

* * * * *

UNITED STATES PATENT AND TRADEMARK OFFICE
CERTIFICATE OF CORRECTION

PATENT NO. : 4,311,644  
DATED : January 19, 1982  
INVENTOR(S) : Jerome L. Moniot et al.

Page 1 of 2

It is certified that error appears in the above—identified patent and that said Letters Patent is hereby corrected as shown below:

Column 1, next to the first structure insert --I--.  
Column 3, structure V should read -- 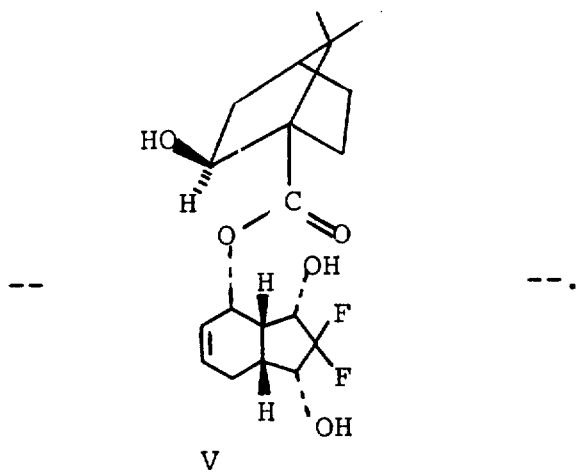 --.

V

Column 5, structure XI should read

-- 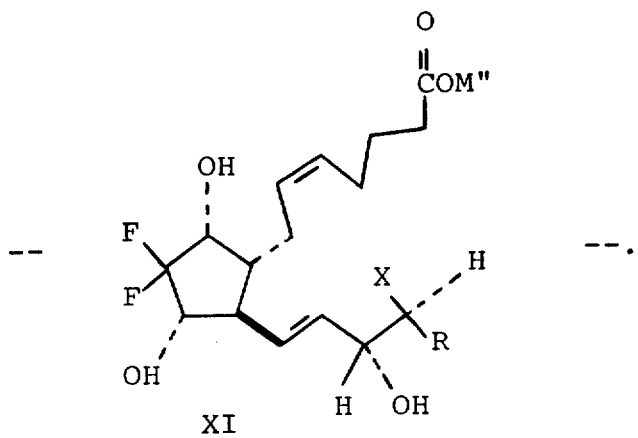 --.

XI

UNITED STATES PATENT AND TRADEMARK OFFICE
CERTIFICATE OF CORRECTION

PATENT NO. : 4,311,644

DATED : January 19, 1982

INVENTOR(S) : Jerome L. Moniot et al.

It is certified that error appears in the above—identified patent and that said Letters Patent is hereby corrected as shown below:

Column 7, line 24, next to the structure insert --B--.
Column 9, line 46, "32%" should read --23%--.
Column 10, line 26, "3A" should read --3$\overset{O}{A}$--.
Column 11, line 30, "$PGF_{2\alpha L}$" should read --$PGF_{2\alpha}$--.
Column 13, the first structure should read

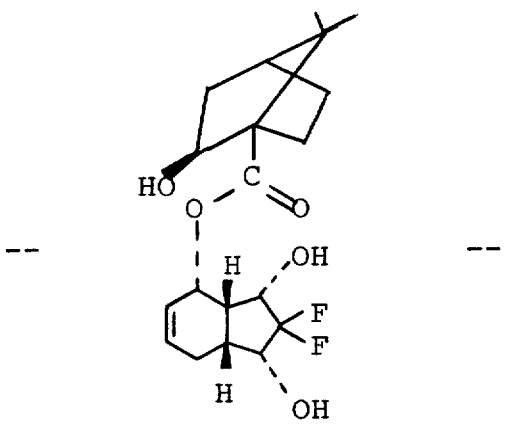

Signed and Sealed this

Eighth Day of June 1982

|SEAL|

Attest:

GERALD J. MOSSINGHOFF

Attesting Officer

Commissioner of Patents and Trademarks